United States Patent [19]

Shiobara et al.

[11] Patent Number: 5,204,119
[45] Date of Patent: Apr. 20, 1993

[54] EXTERNAL PREPARATION COMPRISING CALCIUM SILICATE

[76] Inventors: Takao Shiobara, 20-18, Keyaki 1-chome; Jun Nonaka, 15-4, Midori 1-chome, both of Honjo-shi, Saitama; Masayoshi Kasai, 156, Tsutsujigaoka 5-chome, Kakamigahara-shi, Gifu; Takeshi Konita, 2-2, Fukiagemachihoncho 3-chome, Kitaadachi-gun, Saitama, all of Japan

[21] Appl. No.: 748,208

[22] Filed: Aug. 20, 1991

[30] Foreign Application Priority Data

Aug. 29, 1990 [JP] Japan .................................. 2-228669

[51] Int. Cl.⁵ ...................................... A61K 9/14
[52] U.S. Cl. ..................................... 424/489; 424/449; 424/682; 424/724; 514/420; 514/770; 514/947
[58] Field of Search ................ 424/489, 682, 724, 449

[56] References Cited

U.S. PATENT DOCUMENTS

| | | | |
|---|---|---|---|
| 4,230,765 | 10/1980 | Takahashi et al. | 428/331 |
| 4,493,845 | 1/1985 | Omura et al. | 549/267 |
| 4,638,057 | 1/1987 | Takahashi et al. | 514/781 |
| 4,844,902 | 7/1989 | Grohe | 424/447 |
| 5,071,645 | 12/1991 | Johnson et al. | 514/963 |

FOREIGN PATENT DOCUMENTS 54-89013 7/1979 Japan .
56-84368 7/1981 Japan .

OTHER PUBLICATIONS

Database WPI/Derwent, Accession No. 79-62496B [34], Abstract.
Database WPI/Derwent, Accession No. 81-61506D [34], Abstract.

Primary Examiner—Thurman K. Page
Assistant Examiner—James M. Spear
Attorney, Agent, or Firm—Flynn, Thiel, Boutell & Tanis

[57] ABSTRACT

An external preparation is characterized by comprising calcium silicate. The calcium silicate controls the release rate and percutaneous absorbability of a drug.

7 Claims, 2 Drawing Sheets

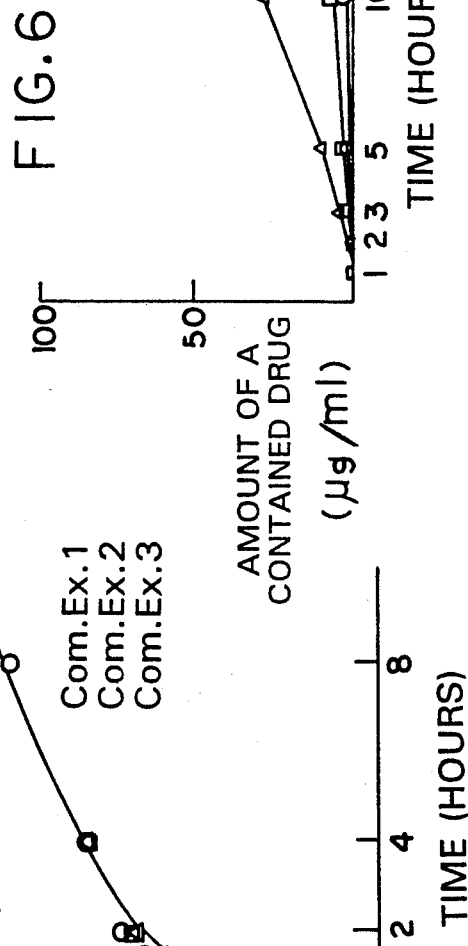
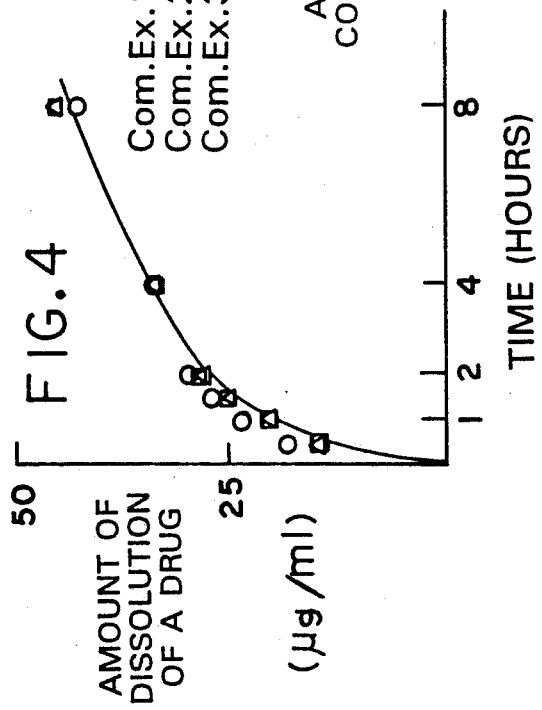
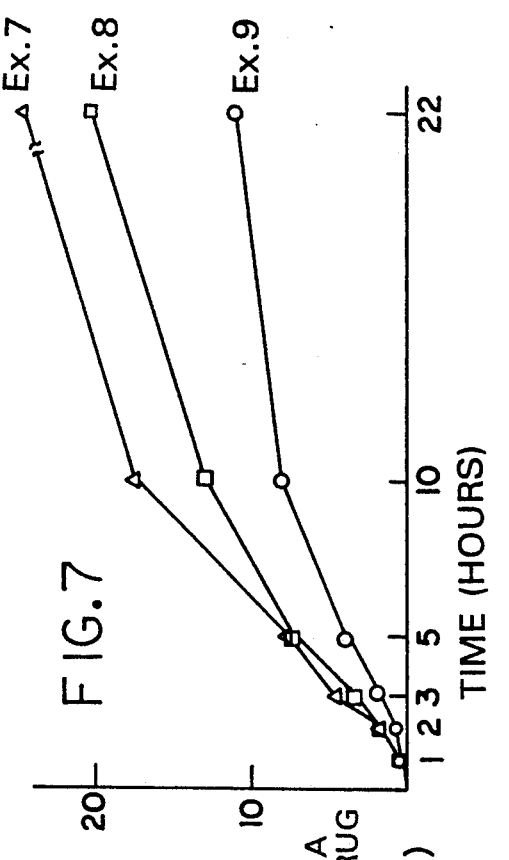
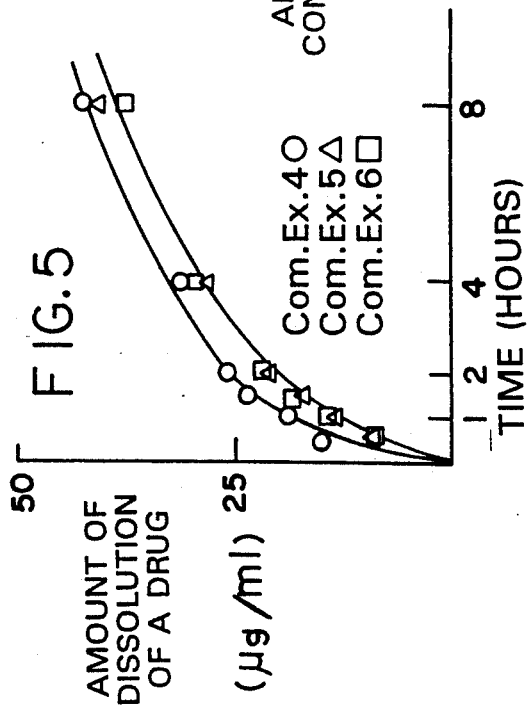

EXTERNAL PREPARATION COMPRISING CALCIUM SILICATE

FIELD OF INDUSTRIAL APPLICATION

The present invention relates to an external application comprising calcium silicate and a drug adsorbed on the calcium silicate and more particularly to an external preparation capable of controlling the release rate and percutaneous absorbability of a drug.

PRIOR ART

Preparations such as ointments or creams and tapes and cataplasms prepared by spreading them to form a sheet have hitherto been used as an external preparation to be applied to the skin. In these preparations, however, unlike other dosage forms such as oral preparations, the skin poses an obstacle in the absorption of the drug and the biological availability thereof is low, so problems occur in the setting of the proper dose of the drug, release of an active ingredient, permeability, and compatibility and miscibility with a base. This has led to studies for a base capable of properly controlling the release of the drug. In view of the above, oleaginous gels such as natural rubber, synthetic rubber, acrylic, cellulose, polysaccharide or silicone gel, or hydrous gels such as water-soluble polymers such as polyvinyl alcohol disclosed in Japanese Patent Laid-Open Nos. 205035/1987 and 218517/1986, etc., have been used as the base for percutaneous administration. These bases, however, have problems such as insufficient percutaneous absorbability, limitation of available drugs and bases, and further, a complicated procedure of formulation.

SUMMARY OF THE INVENTION

An object of the present invention is to provide an external preparation which enables a proper percutaneous absorption effect to be attained through proper control of the release of the drug in a stable state, can be usefully used for a wide variety of drugs, exhibits an excellent effect particularly for a difficulty soluble drug and can be formulated in a very simple procedure.

The present inventors have made intensive studies with a view to solving the above-described problems and, as a result, have found that calcium silicate is highly capable of adsorbing drugs, particularly even difficulty soluble drugs, and exhibits an excellent effect of promoting the dissolution of drugs. They have made further studies based on the above finding and, as a result, have found that the release and percutaneous absorbability of the drug can be controlled by varying the calcium silicate content, which has led to the completion of the present invention.

Accordingly, the present invention relates to an external preparation characterized by comprising calcium silicate and a drug adsorbed on the calcium silicate.

Calcium silicate suitable for use in the present invention is a porous powder. More particularly, calcium silicate particularly suitable for use in the present invention is one having an apparent specific gravity of 0.08 to 0.22, high bulkiness and adsorption capacity, and a gyrolite crystal structure represented by the chemical formula $2CaO \cdot 3SiO_2 \cdot mSiO_2 \cdot nH_2O$, wherein $1 < m < 2$, $2 < n < 3$. Specific examples thereof include calcium silicate in the petal-like form as observed under an electron microscope and/or calcium silicate in the petal-like form as observed under an electron microscope prepared by bonding calcium silicate represented by the above chemical formula to an aqueous solution of a mineral acid, or the above-described types of calcium silicate wherein a lubricant is incorporated or part of the Ca atoms are replaced by Al atoms to reduce the alkalinity. Calcium silicate commercially available from Tokuyama Soda Co., Ltd. under the trade name of "Florite R" is particularly preferred.

The content of calcium silicate in the preparation of the present invention is preferably 1 to 120% by weight, more preferably 10 to 90% by weight, and most preferably 20 to 90% by weight, based on the weight of the drug. When the calcium silicate content is less than 1% by weight, the amount of excess drug which remains unadsorbed on the calcium silicate becomes so large that no more improvement in the control effect can be attained. On the other hand, when the calcium silicate content exceeds 120% by weight, the amount of the drug adsorbed by the calcium silicate is so small that the release of the drug cannot be enhanced.

Although there is no particular limitation on the drug to be used in the present invention as long as it can be percutaneously absorbed, a significant effect of controlling its solubility and releasability can be attained when the drug is a solid substance, in particular a difficulty soluble substance, or an oleaginous substance.

Specific examples of the drug are as follows.

(1) Antipyretic Anti-Inflammatory Analgesics

Indomethacin, ketoprofen, flurbiprofen, acetaminophen, alclofenac, perisoxal citrate, sulidanac, sulpyrine, aluminum flufenamate, tramadol hydrochloride, sulindac, pentazocine, fentiazac, tolmetin sodium, naproxen, fenbufen, pranoprofen, piroxicam, clofezone, pentazocine, dichlofenac sodium, mepirizole, aspirin, aspirin aluminum, acemetacin, amfenac sodium, isopropym antipyrine, ethenzamide, oxaprozin, phenbutazone, camurasin, glafenine, katophenyl butazone, sasapyrine, salicylamide, saridon, diflunisal, suprofen, phenacetin, phenylbutazone, fenoprofen calcium, bucolome, butylon, floctafenine, loxoprofen sodium, dimetotiazine mesylate, butorphanol, eptazocine hydrobromide, choline salicylate, sodium salicylate, thiaramide hydrochloride, metiazinic acid, tinoridine hydrochloride, mefenamic acid, buprenorphine hydrochloride, and benzydamine hydrochloride.

(2) Cardiotonics

Dopamine hydrochloride, dobutamine hydrochloride, ubidecarenone, metildigoxin, aminophylline, caffeine and sodium benzoate, etilefrine hydrochloride, caffeine, carnigen, choline theophyllin, digitoxin, digoxin, diprophylline, G-strophatin, deslanoside and prenylamine lactate.

(3) Narcotic sedatives

Flurazepam, chloral hydrate, nimetazepam, haloxazolam, flurazepam hydrochloride, triazolam, perlapine, estazolam, phenobarbital sodium, amobarbital sodium, ethinamate, potassium bromide, calcium bromide, sodium bromide, secobarbital sodium, nitrazepam, Nervenrch forte, barbital, flunitrazepam, bromovalerylurea, hexobarbital, pentobarbiturate salt and monosodium trichlorethyl phosphate.

(4) Vitamins

Vitamin E group such as α-tocopherol, tocopherol acetate, tocopherol nicotinate, and tocopherol calcium succinate; and vitamin K group such as phytonadione, menatetrenone, menadione, and acetomenaphthone.

There is no particular limitation on the dosage form of the preparation of the present invention, and preferred examples thereof include tapes, plasters, cataplasms, ointments, creams, gels and patches.

The preparation of the present invention may contain a proper base. All of the base ingredients commonly used as a preparation for percutaneous administration may be used, and the base may be any of oleaginous base ingredients and aqueous base ingredients. Examples of the oleaginous base ingredients include white petrolatum, purified lanolin, liquid paraffin, vegetable oils, squalane, silicone and waxes. Examples of the aqueous bases include water, lower alcohols, polyhydric alcohols and water-soluble polymers. It is also possible to use base ingredients commonly used as a patch, and examples thereof include adhesive materials, such as natural rubbers, synthetic rubbers, styrene-isoprene-styrene copolymers, polyacrylic ester resins and polyisobutylene resins, and polymer compositions, such as soft polyamide resin, polyvinyl alcohol and polyacrylic resin.

Besides the above-described components, tackifiers, surfactants, stabilizers, preservatives and antiseptics may be properly incorporated in the preparation of the present invention.

When the preparation of the present invention is, for example, a tape, it can be prepared by making a drug adsorbed by calcium silicate to prepare a powder, mixing the powder with the base or other additives, and spreading the mixture on a sheet to prepare a tape.

In this case, the release of the drug can be controlled by varying the amount of calcium silicate based on the weight of the drug. Specifically, in the case of indomethacin, the release of the drug can be enhanced by increasing the amount of calcium silicate, though the releasability varies depending upon the drug. By contrast, in the case of ketoprofen and flurbiprofen, the release of the drug is enhanced by reducing the amount of calcium silicate. In any event, the control can be very simply conducted through the utilization of the releasability of the drug.

The external preparation of the present invention is excellent in the adsorption of the drug and enables the releasability and percutaneous absorbability of the drug to be easily controlled by varying the amount of calcium silicate.

Further, it can be prepared by a very simple process wherein a drug is adsorbed on calcium silicate, so that the drug can be held and released in a stable state without causing any lowering in the activity of the drug and the safety to a living body is high by virtue of less irritant action.

Further, it is applicable to a wide variety of drugs, particularly suitable for an improvement in the dissolution of a solid or oleaginous drug, and can be advantageously applicable to a difficulty soluble drug as well.

BRIEF DESCRIPTION OF THE DRAWINGS

FIG. 4 is a graph showing the relationship between the content of Carplex in tapes prepared in Comparative Examples 1 to 3 and the amount of dissolution of the drug contained in the tapes;

FIG. 5 is a graph showing the relationship between the content of Aerosil in tapes prepared in Comparative Examples 4 to 6 and the amount of dissolution of the drug contained in the tapes;

FIG. 6 is a graph showing the relationship between the content of Florite R in tapes prepared in Examples 4 to 6 and the skin penetration of the drug contained in the tapes; and FIG. 7 is a graph showing the relationship between the content of Florite R in tapes prepared in Examples 7 to 9 and the skin penetration of the drug contained in the tapes.

EXAMPLES

Figure 1:
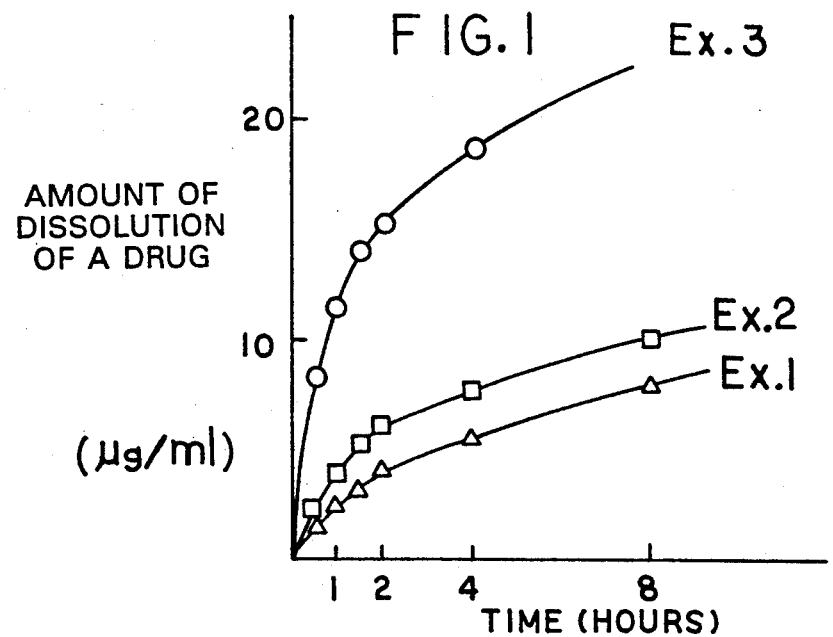
FIG. 1 is a graph showing the relationship between the content of Florite R in tapes prepared in Examples 1 to 3 and the amount of dissolution of the drug contained in the tapes.

The present invention will now be described in more detail by referring to the following Examples, though it is not limited to these Examples only.

EXAMPLE 1

Base ingredients described below as base formulation 1 were put in a mixer (manufactured by Moriyama Seisakusho Co., Ltd.), mixed and melted by heating to prepare a base. 78 parts by weight of the base was put in the mixer and melted by heating. Separately, 21 parts by weight of indomethacin (hereinafter abbreviated to "IND") was added to 1 part by weight of Florite R, diethyl ether was added thereto to dissolve IND in diethyl ether, and diethyl ether was removed by vacuum distillation to prepare a powder comprising IND adsorbed on Florite R. The powder was put in the mixer for mixing, and the mixture was spread on a sheet to prepare a tape containing 1% by weight of Florite R.

| Base formulation 1: | |
|---|---|
| SIS copolymer (a product of Shell Chemical Co., Ltd.) | 44.6% by weight |
| Arkon P100 (a product of Arakawa Chemical Industries, Ltd.) | 13.4% by weight |
| polybutene | 8.9% by weight |
| liquid paraffin | 31.3% by weight |
| dibutylhydroxytoluene | 1.8% by weight |
| | 100.0% by weight |

EXAMPLE 2

Base ingredients described above as base formulation 1 were put in a mixer (manufactured by Moriyama Seisakusho Co., Ltd.), mixed and melted by heating to prepare a base. 76 parts by weight of the base was put in the mixer and melted by heating. Separately, 21 parts by weight of IND was added to 3 parts by weight of Florite R, diethyl ether was added thereto to dissolve IND in diethyl ether, and diethyl ether was removed by vacuum distillation to prepare a powder comprising IND adsorbed on Florite R. The powder was put in the mixer for mixing, and the mixture was spread on a sheet to prepare a tape containing 3% by weight of Florite R.

EXAMPLE 3

Base ingredients described above as base formulation 1 were put in a mixer (manufactured by Moriyama Seisakusho Co., Ltd.), mixed and melted by heating to prepare a base. 73 parts by weight of the base was put in the mixer and melted by heating. Separately, 21 parts by weight of IND was added to 6 parts by weight of Florite R, diethyl ether was added thereto to dissolve IND in diethyl ether, and diethyl ether was removed by vacuum distillation to prepare a powder comprising IND adsorbed on Florite R. The powder was put in the mixer for mixing, and the mixture was spread on a sheet to prepare a tape containing 6% by weight of Florite R.

EXAMPLE 4

Base ingredients described above as base formulation 1 were put in a mixer (manufactured by Moriyama Seisakusho Co., Ltd.), mixed and melted by heating to prepare a base. 92 parts by weight of the base was put in the mixer and melted by heating. Separately, 7 parts by weight of ketoprofen (hereinafter referred to as "KET") was added to 1 part by weight of Florite R, diethyl ether was added thereto to dissolve KET in diethyl ether, and diethyl ether was removed by vacuum distillation to prepare a powder comprising KET adsorbed on Florite R. The powder was put in the mixer for mixing, and the mixture was spread on a sheet to prepare a tape containing 1% by weight of Florite R.

EXAMPLE 5

Base ingredients described above as base formulation 1 were put in a mixer (manufactured by Moriyama Seisakusho Co., Ltd.), mixed and melted by heating to prepare a base. 90 parts by weight of the base was put in the mixer and melted by heating. Separately, 7 parts by weight of KET was added to 3 parts by weight of Florite R, diethyl ether was added thereto to dissolve KET in diethyl ether, and diethyl ether was removed by vacuum distillation to prepare a powder comprising KET adsorbed on Florite R. The powder was put in the mixer for mixing, and the mixture was spread on a sheet to prepare a tape containing 3% by weight of Florite R.

EXAMPLE 6

Base ingredients described above as base formulation 1 were put in a mixer (manufactured by Moriyama Seisakusho Co., Ltd.), mixed and melted by heating to prepare a base. 87 parts by weight of the base was put in the mixer and melted by heating. Separately, 7 parts by weight of KET was added to 6 parts by weight of Florite R, diethyl ether was added thereto to dissolve KET in diethyl ether, and diethyl ether was removed by vacuum distillation to prepare a powder comprising KET adsorbed on Florite R. The powder was put in the mixer for mixing, and the mixture was spread on a sheet to prepare a tape containing 6% by weight of Florite R.

EXAMPLE 7

Base ingredients described above as base formulation 1 were put in a mixer (manufactured by Moriyama Seisakusho Co., Ltd.), mixed and melted by heating to prepare a base. 90 parts by weight of the base was put in the mixer and melted by heating. Separately, 9 parts by weight of flurbiprofen (hereinafter referred to as "FLU") was added to 1 part by weight of Florite R, diethyl ether was added thereto to dissolve FLU in diethyl ether, and diethyl ether was removed by vacuum distillation to prepare a powder comprising FLU adsorbed on Florite R. The powder was put in the mixer for mixing, and the mixture was spread on a sheet to prepare a tape containing 1% by weight of Florite R.

EXAMPLE 8

Base ingredients described above as base formulation 1 were put in a mixer (manufactured by Moriyama Seisakusho Co., Ltd.), mixed and melted by heating to prepare a base. 88 parts by weight of the base was put in the mixer and melted by heating. Separately, 9 parts by weight of FLU was added to 3 parts by weight of Florite R, diethyl ether was added thereto to dissolve FLU in diethyl ether, and diethyl ether was removed by vacuum distillation to prepare a powder comprising FLU adsorbed on Florite R. The powder was put in the mixer for mixing, and the mixture was spread on a sheet to prepare a tape containing 3% by weight of Florite R.

EXAMPLE 9

Base ingredients described above as base formulation 1 were put in a mixer (manufactured by Moriyama Seisakusho Co., Ltd.), mixed and melted by heating to prepare a base. 85 parts by weight of the base was put in the mixer and melted by heating. Separately, 9 parts by weight of FLU was added to 6 parts by weight of Florite R, diethyl ether was added thereto to dissolve FLU in diethyl ether, and diethyl ether was removed by vacuum distillation to prepare a powder comprising FLU adsorbed on Florite R. The powder was put in the mixer for mixing, and the mixture was spread on a sheet to prepare a tape containing 6% by weight of Florite R.

For comparison with the products of the present invention, tapes were prepared through the use of Aerosil which is a silicic anhydride and Carplex which is a silicic anhydride hydrate instead of Florite R in varied amounts. These will be described below as Comparative Examples 1 to 6.

COMPARATIVE EXAMPLE 1

Base ingredients described above as base formulation 1 were put in a mixer (manufactured by Moriyama Seisakusho Co., Ltd.), mixed and melted by heating to prepare a base. 92 parts by weight of the base was put in the mixer and melted by heating. Separately, 7 parts by weight of KET was added to 1 part by weight of Carplex, diethyl ether was added thereto to dissolve KET in diethyl ether, and diethyl ether was removed by vacuum distillation to prepare a powder comprising KET adsorbed on Carplex. The powder was put in the mixer for mixing, and the mixture was spread on a sheet to prepare a tape containing 1% by weight of Carplex.

COMPARATIVE EXAMPLE 2

Base ingredients described above as base formulation 1 were put in a mixer (manufactured by Moriyama Seisakusho Co., Ltd.), mixed and melted by heating to prepare a base. 90 parts by weight of the base was put in the mixer and melted by heating. Separately, 7 parts by weight of KET was added to 3 parts by weight of Carplex, diethyl ether was added thereto to dissolve KET in diethyl ether, and diethyl ether was removed by vacuum distillation to prepare a powder comprising KET adsorbed on Carplex. The powder was put in the mixer for mixing, and the mixture was spread on a sheet to prepare a tape containing 3% by weight of Carplex.

COMPARATIVE EXAMPLE 3

Base ingredients described above as base formulation 1 were put in a mixer (manufactured by Moriyama Seisakusho Co., Ltd.), mixed and melted by heating to prepare a base. 87 parts by weight of the base was put in the mixer and melted by heating. Separately, 7 parts by weight of KET was added to 6 parts by weight of Carplex, diethyl ether was added thereto to dissolve KET in diethyl ether, and diethyl ether was removed by vacuum distillation to prepare a powder comprising KET adsorbed on Carplex. The powder was put in the mixer for mixing, and the mixture was spread on a sheet to prepare a tape containing 6% by weight of Carplex.

COMPARATIVE EXAMPLE 4

Base ingredients described above as base formulation 1 were put in a mixer (manufactured by Moriyama Seisakusho Co., Ltd.), mixed and melted by heating to prepare a base. 92 parts by weight of the base was put in the mixer and melted by heating. Separately, 7 parts by weight of KET was added to 1 part by weight of Aerosil, diethyl ether was added thereto to dissolve KET in diethyl ether, and diethyl ether was removed by vacuum distillation to prepare a powder comprising KET adsorbed on Aerosil. The powder was put in the mixer for mixing, and the mixture was spread on a sheet to prepare a tape containing 1% by weight of Aerosil.

COMPARATIVE EXAMPLE 5

Base ingredients described above as base formulation 1 were put in a mixer (manufactured by Moriyama Seisakusho Co., Ltd.), mixed and melted by heating to prepare a base. 90 parts by weight of the base was put in the mixer and melted by heating. Separately, 7 parts by weight of KET was added to 3 parts by weight of Aerosil, diethyl ether was added thereto to dissolve KET in diethyl ether, and diethyl ether was removed by vacuum distillation to prepare a powder comprising KET adsorbed on Aerosil. The powder was put in the mixer for mixing, and the mixture was spread on a sheet to prepare a tape containing 3% by weight of Aerosil.

COMPARATIVE EXAMPLE 6

Base ingredients described above as base formulation 1 were put in a mixer (manufactured by Moriyama Seisakusho Co., Ltd.), mixed and melted by heating to prepare a base. 87 parts by weight of the base was put in the mixer and melted by heating. Separately, 7 parts by weight of KET was added to 6 parts by weight of Aerosil, diethyl ether was added thereto to dissolve KET in diethyl ether, and diethyl ether was removed by vacuum distillation to prepare a powder comprising KET adsorbed on Aerosil. The powder was put in the mixer for mixing, and the mixture was spread on a sheet to prepare a tape containing 6% by weight of Aerosil.

TEST EXAMPLE

The dissolution of drug was evaluated on tapes prepared in Examples 1 to 9 and Comparative Examples 1 to 6 by the following method. Further, the skin penetration of the drug was evaluated on the tapes prepared in Examples 4 to 9 by the following method.

TEST ON DISSOLUTION OF DRUG

The dissolution of the drug was evaluated on the tapes prepared in Examples 1 to 9 and Comparative Examples 1 to 6 through the use of an apparatus described in Method 2 (paddle method) of Dissolution Test specified in the Pharmacopoeia of Japan (11th edition). At the outset, a test piece having an area of 50 cm$^2$ was prepared from the tape, the support of the tape was fixed to a stainless steel fixture, and a release paper on the medicated layer was removed. 500 ml of a buffer solution (pH 5.5) was put in a measuring vessel, and the stainless steel fixture was sunk on the bottom of the vessel in such a manner that the medicated layer of the tape faces upwards. The buffer solution was kept at 32° C. and allowed to stand for a given period of time while rotating the paddle at 100 rpm. Then, the amount of the drug dissolved into the buffer solution was measured, and a change in the amount of dissolution of the drug with time was determined. The results are given in FIGS. 1 to 5.

TEST ON SKIN PENETRATION OF DRUG

A grained extirpated skin of a male SD rat (weight: 220 to 250 g, age: 8 weeks) was fixed to an in vitro diffusion cell in such a manner that the epidermal side served as a donor side, and tapes prepared in Examples 4 to 9 were put on the donor side. 50 ml of a buffer solution (pH: 5.5) was used as a receptor solution and kept in an incubator at 37° C. The receptor solution was stirred with a stirrer, sampled in an amount of 0.5 ml at given time intervals, and subjected to quantitative determination of the drug. The quantitative determination was conducted by high performance liquid chromatography. The results are given in FIGS. 6 and 7.

RESULTS

It is apparent from FIG. 1 that the amount of dissolution of indomethacin in the tapes prepared in Examples 1, 2 and 3 as an external patch of the present invention remarkably increased with an increase in the amount of Florite R. Further, the dissolution pattern obtained was such that the amount of dissolution was proportional to the amount of addition of Florite R. Therefore, it is apparent that the release of indomethacin can be controlled by the amount of addition of Florite R.

Figure 2:
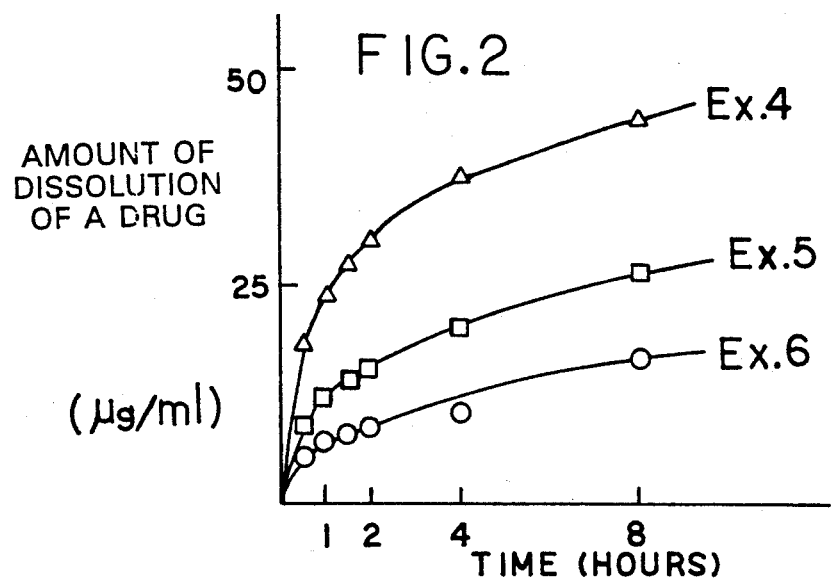
FIG. 2 is a graph showing the relationship between the content of Florite R in tapes prepared in Examples 4 to 6 and the amount of dissolution of the drug contained in the tapes.

As is apparent from FIGS. 2, 4 and 5, in the tapes prepared in Examples 4, 5 and 6 as an external patch of the present invention, the dissolution pattern obtained was such that the amount of dissolution of ketoprofen was inversely proportional to the amount of addition of Florite. On the other hand, in Comparative Examples 1 to 3 and Comparative Examples 4 to 6, no significant change caused by the variation in the amount of addition of Florite R was observed, and similar dissolution patterns were obtained. Therefore, it is apparent that the release of the ketoprofen can be controlled by the amount of addition of Florite R. It has thus become apparent that even in the same silicate compounds, Carplex and Aerosil exhibit no release control effect.

Figure 3:
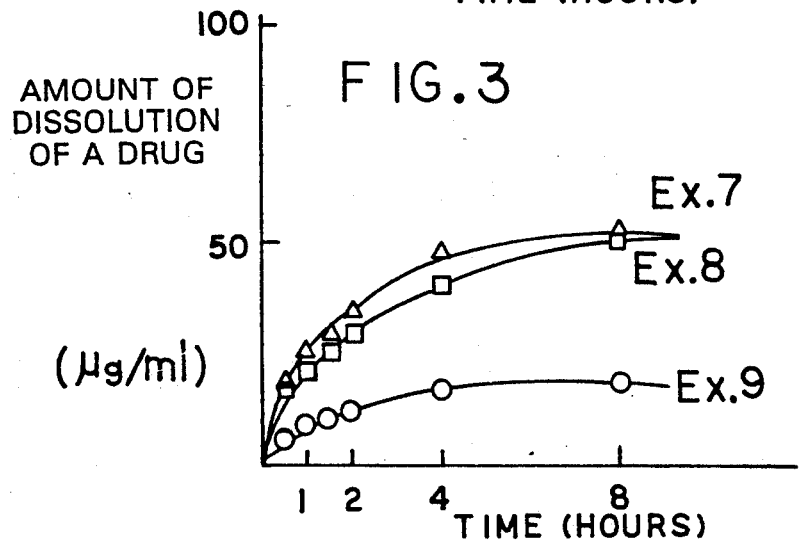
FIG. 3 is a graph showing the relationship between the content of Florite R in tapes prepared in Examples 7 to 9 and the amount of dissolution of the drug contained in the tapes.

As is apparent from FIG. 3, in the tapes prepared in Examples 7, 8 and 9 as an external patch of the present invention, the dissolution pattern obtained was such that the amount of dissolution of flurbiprofen was inversely proportional to the amount of addition of Florite R. Therefore, it is apparent that the release of flurbiprofen can be controlled by the amount of addition of Florite R.

As is apparent from FIGS. 6 and 7, in the tapes prepared in Examples 4 to 6 and Examples 7 to 9 as an external patch of the present invention, the skin penetration of each of the ketoprofen and flurbiprofen was inversely proportional to the amount of addition of Florite R. Therefore, it is apparent that the percutaneous absorption can be controlled by the amount of addition of Florite R.

We claim:

1. An external preparation comprising calcium silicate in the form of a porous powder and a drug adsorbed thereon, said calcium silicate having a gyrolite crystal structure having the formula $2CaO \cdot 3SiO_2 \cdot mSiO_2 \cdot nH_2O$, with $1 < m < 2$ and $2 < n < 3$ and is contained in the preparation in an amount of from 1 to 120 percent by weight based on the weight of the drug.

2. The external preparation of claim 1, wherein said drug is ketoprofen.

3. The external preparation of claim 1, wherein said drug is flurbiprofen.

4. The external preparation of claim 1, wherein said drug is indomethacin.

5. The external preparation of claim 1, wherein said calcium silicate has an apparent specific gravity of from 0.08 to 0.22.

6. The external preparation of claim 1, wherein the calcium silicate is contained in the preparation in an amount of from 10 to 90 percent by weight.

7. The external preparation of claim 1, wherein the calcium silicate is contained in the preparation in an amount of from 20 to 90 percent by weight.

* * * * *